(12) United States Patent
Kunishima

(10) Patent No.: US 7,462,715 B2
(45) Date of Patent: Dec. 9, 2008

(54) DEHYDRATING CONDENSATION AGENT HAVING PROPERTY OF ACCUMULATING AT INTERFACE WITH WATER

(75) Inventor: Munetaka Kunishima, Kobe (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/588,940

(22) PCT Filed: Jan. 31, 2005

(86) PCT No.: PCT/JP2005/001733

§ 371 (c)(1),
(2), (4) Date: Aug. 8, 2006

(87) PCT Pub. No.: WO2005/075442

PCT Pub. Date: Aug. 18, 2005

(65) Prior Publication Data

US 2007/0135632 A1    Jun. 14, 2007

(30) Foreign Application Priority Data

Feb. 10, 2004  (JP)  ............... 2004-033284

(51) Int. Cl.
- *C07D 251/46* (2006.01)
- *C07C 67/08* (2006.01)
- *C07C 69/24* (2006.01)
- *C07C 231/02* (2006.01)
- *C07C 233/05* (2006.01)

(52) U.S. Cl. ................ 544/219; 560/1; 560/8
(58) Field of Classification Search .............. 544/219; 560/1, 8
See application file for complete search history.

(56) References Cited

U.S. PATENT DOCUMENTS

| | | | | |
|---|---|---|---|---|
| 6,458,948 | B1 * | 10/2002 | Iwasaki et al. | ............... 540/219 |
| 2003/0153785 | A1 | 8/2003 | Hirano et al. | |
| 2003/0181753 | A1 | 9/2003 | Groger et al. | |

FOREIGN PATENT DOCUMENTS

| | | |
|---|---|---|
| EP | 1085000 A1 | 3/2001 |
| JP | 2001-247555 | 9/2001 |
| JP | 2004-503522 | 2/2004 |
| WO | WO 00/53544 | 9/2000 |

OTHER PUBLICATIONS

International Search Report, PCT/JP2005/001733, Apr. 19, 2005.
International Preliminary Examination Report, PCT/JP2005/001733, Dec. 21, 2005.
Kunishima, et al., Cyclodextrin-Based Artificial Acyltransferase: Substrate-Specific Catalytic Amidation of Carboxylic Acids in Aqueous Solvent, Journal of American Chemical Society, vol. 123,No. 43, pp. 10760-10761, 2001 Japan.

Nozaki, Efficient Amounts of Additives for Peptide Coupling Mediated by a Water-Soluble Carbodiimide in Aqueous Media, Chemistry Letters, 1997, pp. 1-2.
Kunishima et al., Formation of Carboxamides by Direct Condensation of Carboxylic Acids and Amines in Alcohols Using a New Alcohol-and Water-Soluble Condensing Agent: DMT-MM, Tetrahedron, 2001, vol. 57, pp. 1551-1558.
Ranganathan et al., Journal of the American Chemical Society, 1989, vol. 111, pp. 1144-1145.
Rico et al., Effect of Micelles on Cyclization Reactions: The Use of N-Hexadecyl-2-choropyridinium Iodide as an Amphiphilic Carboxyl-Activating Agent in Lactonization and Lactamization, Journal of Organic Chemistry, 1994, vol. 59, pp. 415-420.
Manabe at al., Dehydration Reactions in Water, Surfactant-Type Bronsted Acid-Catalyzed Direct Esterfication of Carboxylic Acids with Alcohols in an Emulsion System, Journal of the American Chemical Society, 2001, vol. 123, pp. 10101-10102.
Kunishima et al., Approach to Green Chemistry of DMT-MM: Recovery and Recycle of Coproduct to Chloromethane-free DMT-MM, Tetrahedron Letters, 2002, vol. 43, pp. 3323-3326.
Kunishima at al., 4-(4,6-Dimethoxy-1,3,5,-triazin-2-yl)-4-methylmorpholinium Chloride: An Efficient Condensing Agent Leading to the Formation of Amides and Esters, Tetrahedron, 1999, vol. 55, pp. 13159-13170.

(Continued)

*Primary Examiner*—Venkataraman Balasubramanian
(74) *Attorney, Agent, or Firm*—Amin, Turocy & Calvin, LLP

(57) ABSTRACT

The present invention provides a 1,3,5-triazine compound represented by the following formula I:

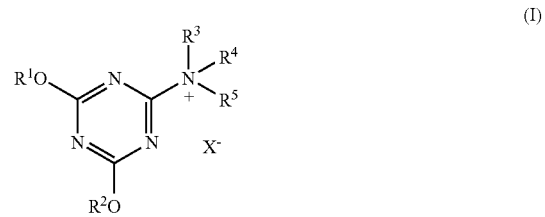

This compound can be synthesized easily and more economically and can be used as a dehydrating condensing agent having the property of accumulating at a water interface. In the case where carboxylic acid, amine, alcohol or other reaction substrate is amphiphilic, when mixing the dehydrating condensing agent of the present invention, which is amphiphilic, and the substrate to form various molecular aggregate phase including micelles in an aqueous solution, the substrate and the dehydrating condensing agent can be accumulated at the water interface. As a result, the concentration of the substrate increases locally at the water interface, and condensation reaction can be performed extremely efficiently.

18 Claims, No Drawings

OTHER PUBLICATIONS

Jaeger D.A. and Ippoliti, J.T., Effect of Inverse Micelles on the Competition Between Lactonization and Polymerization Reactions of an w-Hydroxy Carboxylic Acid, Journal of Organic Chemistry, 1981, vol. 46, pp. 4964-4968.

Manabe at al., Dehydration Reactions in Water. Bronsted Acid-Surfactant-Combined Catalyst for Ester, Ether, Thioether, and Dithioacetal Formation in Water, Journal of the American Chemical Society, 2002, vol. 124, pp. 11971-11978.

* cited by examiner

DEHYDRATING CONDENSATION AGENT HAVING PROPERTY OF ACCUMULATING AT INTERFACE WITH WATER

TECHNICAL FIELD

The present invention relates to a dehydrating condensing agent that can be used at a water interface. More specifically, the present invention relates to a dehydrating condensing agent capable of accumulating at a water interface that can be used in production of carboxylic acid derivatives.

BACKGROUND ART

Carboxylic acid derivatives, in particular, amide compounds having carboxamide groups (—CONH—) are important compounds for pharmaceuticals, agricultural chemicals, dyes, high-molecular weight compounds or the like. Therefore, various synthetic methods thereof have been examined. For example, there is a method for producing amide compounds by dehydrating condensation of carboxylic acids and amine compounds in a water-containing solvent. However, in this case, the reaction in a water-containing solvent proceeds in a low yield, so that it is common to activate the carboxyl groups in an anhydrous solvent and then perform a reaction with amines.

In recent years, carbodiimide derivatives have been developed as a condensing agent that can be used in an aqueous solvent (Nozaki, Chemistry Letters, 1997, pp. 1-2). This is a method of synthesizing peptides in a water-containing solvent by using 1-ethyl-3-(3-dimethylaminopropyl) carbodiimide (EDC) as a condensing agent. As a condensing agent that can be used in water or alcohols, 4-(4,6-dimethoxy-1,3,5-triazin-2-yl)-4-methylmorpholinium chloride (DMT-MM) has been reported (Kunishima et al., Tetrahedron, 2001, vol. 57, pp. 1551-1558), and this is used for production of amide compounds or ester compounds (International Application Publication No. WO/0053544). However, EDC and DMT-MM are both water-soluble and are condensing agents that are used in a uniform solvent system containing water. Therefore, it is not suitable to use them with a water-insoluble substrate.

On the other hand, a method for synthesizing peptides using a carbodiimide having a long chain alkyl group as a condensing agent at a reverse micelle interface between a hydrophobic solvent and water has been reported (Ranganathan et al., Journal of the American Chemical Society, 1989, vol. 111, pp. 1144-1145). Another method of dehydrating condensation at a micelle interface, which is lactonization and lactamization using amphiphilic Mukaiyama reagent (N-alkyl halopyridinium salt), has been reported (Rico et al., Journal of Organic Chemistry, 1994, vol. 59, pp. 415-420). However, all of these methods provide poor yields. Alternatively, it has been reported that esterification can be performed with Lewis acid thermodynamically in a hydrophobic field that is formed in an acid aqueous solution (Kobayashi at al., Journal of the American Chemical Society, 2001, vol. 123, pp. 10101). Since this reaction also proceeds even in the absence of water, the reaction is not performed at the interface. Accordingly, it cannot be said that the characteristics of the interface are utilized in the reaction. Thus, at present, other than the above agent, there is almost no condensing agent that can be used for dehydrating condensation of carboxylic acid at a water interface, which limits the type of carboxylic acids that can be utilized.

DISCLOSURE OF INVENTION

It is an object of the present invention to provide a dehydrating condensing agent having the property of accumulating at water interface that can be easily synthesized and is more economical.

Based on the fact that DMT-MM, which is a dehydrating condensing agent that can be used in water, which is described in Kunishima at el., Tetrahedron, 2001, vol. 57, pp. 1551-1558, has a hydrophilic quaternary ammonium structure, an amphiphilic compound having the property of accumulating specifically at a water interface was obtained by introducing a hydrophobic group such as a long chain alkyl group into a compound having a DMT-MM-like structure,.

The present invention provides a 1,3,5-triazine compound represented by the following formula I:

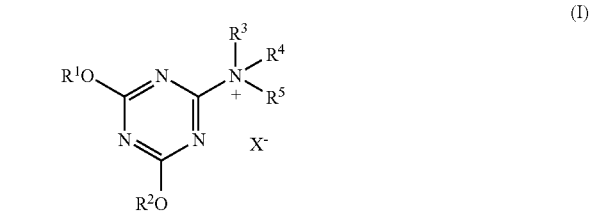

(I)

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear; and $X^-$ is a halide ion, a triflate anion, a nitrate ion, a sulfate ion, a hydrogensulfate ion, a sulfonate ion, a tetrafluoroborate ion, or a perchlorate ion.

In a preferred embodiment, at least one of $R^1$ and $R^2$ is a methyl group or an ethyl group.

In a more preferred embodiment, n is 12 to 16.

The present invention also provides a method for producing a 1,3,5-triazine compound represented by the following formula I':

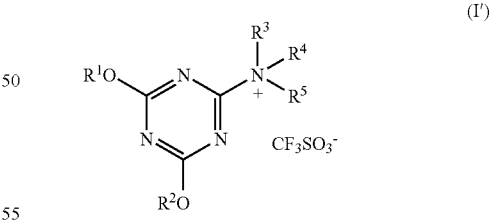

(I')

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear; and $X^-$ is a triflate anion, the method comprises:

obtaining triflate by mixing a compound represented by the following formula II and trifluoromethanesulfonic anhydride in an organic solvent:

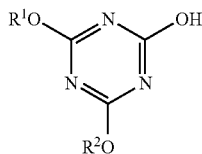

(II)

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R_1$ and $R^2$ are not alkyl groups having 6 to 20 carbon atoms at the same time; and mixing the obtained triflate and a tertiary amine represented by the following formula III in an appropriate organic solvent:

(III)

wherein one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear.

The present invention further provides a method for producing a 1,3,5-triazine compound represented by the following formula I'':

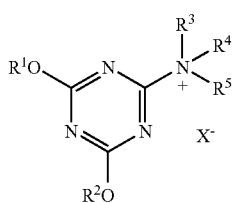

(I'')

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear; and $X^-$ is a halide ion, the method comprises:

mixing a compound represented by the following formula IV and a tertiary amine represented by the following formula III in an appropriate solvent:

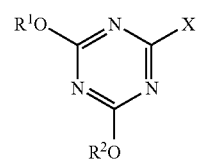

(IV)

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; and X is a halogen atom;

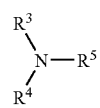

(III)

wherein one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear.

The present invention provides a method for producing a carboxylic acid derivative, the method comprises:

mixing a carboxylic acid and a compound having a nucleophilic functional group in an aqueous solution in the presence of a 1,3,5-triazine compound represented by the following formula I:

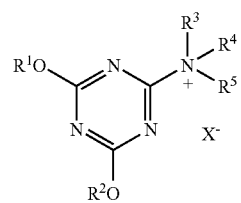

(I)

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+$ $(CH_3)_3)$, $-CH_2CH_2SO_3^-$, $-CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently $-CH_2COO-C_nH_{2n+1}$, $-C_nH_{2n+1}$, or $-C_6H_4$-p-$C_nH_{2n+1}$, where n is an integer of 6 to 20, and $-C_nH_{2n+1}$ is linear; and $X^-$ is a halide ion, a triflate anion, a nitrate ion, a sulfate ion, a hydrogensulfate ion, a sulfonate ion, a tetrafluoroborate ion, or a perchlorate ion.

In a preferred embodiment, the carboxylic acid is a fatty acid having 6 to 20 carbon atoms.

In a more preferred embodiment, the carboxylic acid is a fatty acid having 8 to 18 carbon atoms.

In another preferred embodiment, at least one of $R^1$ and $R^2$ in the formula I is a methyl group or an ethyl group.

In a further preferred embodiment, n in the formula I is 12 to 16.

In a preferred embodiment, the compound having a nucleophilic functional group is a primary amine compound or a secondary amine compound.

The present invention also provides another method for producing a carboxylic acid derivative, the method comprises mixing:
 a carboxylic acid;
 a compound having a nucleophilic functional group;
 a compound represented by the following formula IV; and
 a tertiary amine represented by the following formula III in an aqueous solution:

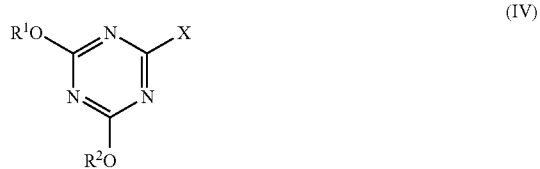

(IV)

wherein $R^1$ and $R^2$ are each independently a methyl group, an ethyl group, a hydroxyalkyl group having 2 to 5 carbon atoms, $-(CH_2CH_2O)_mR^6$ (where m is an integer of 1 to 120, and $R^6$ is a hydrogen atom, a methyl group, an ethyl group, or a propyl group), $-(CH_2CH_2NR^7)_mH$ (where m is an integer of 1 to 120, and $R^7$ is an alkyl group having 2 to 5 carbon atoms, an N,N-dialkylaminoethyl group or $-CH_2CH_2N^+(CH_3)_3)$, $-CH_2CH_2SO_3^-$, $-CH_2CH_2N^+(CH_3)_3$, or an alkyl group having 6 to 20 carbon atoms, but both $R^1$ and $R^2$ are not alkyl groups having 6 to 20 carbon atoms at the same time; and X is a halogen atom,

(III)

wherein one or two of $R^3$, $R^4$ and $R^5$ are methyl groups, and the remaining $R^3$, $R^4$ and $R^5$ are each independently $-CH_2COO-C_nH_{2n+1}$, $-C_nH_{2n+1}$, or $-C_6H_4$-p-$C_nH_{2n+1}$, where n is an integer of 6 to 20, and $-C_nH_{2n+1}$ is linear.

In a preferred embodiment, the carboxylic acid is a fatty acid having 6 to 20 carbon atoms.

In a more preferred embodiment, the carboxylic acid is a fatty acid having 8 to 18 carbon atoms.

In another preferred embodiment, at least one of $R^1$ and $R^2$ in the formula I is a methyl group or an ethyl group.

In a further preferred embodiment, n in the formula I is 12 to 16.

In a preferred embodiment, the compound having a nucleophilic functional group is a primary amine compound or secondary amine compound.

In a preferred embodiment, the compound having a nucleophilic functional group is an alcohol compound.

In the case where a reaction substrate is amphiphilic, by mixing the amphiphilic dehydrating condensing agent of the present invention and the reaction substance to form micelles in aqueous solution, the substrate and the dehydrating condensing agent can be accumulated at the water interface. As a result, the concentration of the substrate increases locally at the water interface, and the molecular motion (in particular, three-dimensional translation and isotropic rotation) is suppressed, so that the reaction is accelerated, and selectivity is improved. Therefore, when carboxylic acids, amines, alcohols or the like, which is a substrate, are converted to amphiphilic derivatives, all the reaction sites are accumulated at the interface. Thus, with the dehydrating condensing agent of the present invention, the condensation reaction can be performed very efficiently. Furthermore, the dehydrating condensing agent of the present invention can be synthesized easily, and therefore is cost-efficient.

BEST MODE FOR CARRYING OUT THE INVENTION

The dehydrating condensing agent of the present invention is a 1,3,5-triazine compound represented by the following formula I:

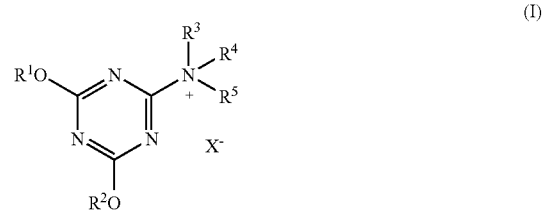

(I)

In the formula I, $R^1$ and $R^2$ are each independently a methyl group, an ethyl group, a hydroxyalkyl group having 2 to 5 carbon atoms, 13 $(CH_2CH_2O)_mR^6$ (where m is an integer of 1 to 120, and $R^6$ is a hydrogen atom, a methyl group, an ethyl group, or a propyl group), $-(CH_2CH_2NR^7)_mH$ (where m is an integer of 1 to 120, and $R^7$ is an alkyl group having 2 to 5 carbon atoms, an N,N-dialkylaminoethyl group or $-CH_2CH_2N^+(CH_3)_3)$, $-CH_2CH_2SO_3^-$, $-CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently $-CH_2COO-C_nH_{2n+1}$, $-C_nH_{2n+1}$, or $-C_6H_4$-p-$C_nH_{2n+1}$, where n is an integer of 6 to 20, and $-C_nH_{2n+1}$ is linear; and $X^-$ is a halide ion, a triflate anion ($CF_3SO_3^-$), a nitrate ion ($NO_3^-$), a sulfate ion ($1/2SO_4^-$), a hydrogensulfate ion ($HSO_4^-$), a sulfonate ion ($RSO_3^-$), a tetrafluoroborate ion ($BF_4^-$), or a perchlorate ion ($ClO_4^-$).

In the formula I, when $R^1$ and $R^2$ are hydroxyalkyl groups having 2 to 5 carbon atoms, the hydroxyalkyl groups can be linear, branched or cyclic, and there is no particular limitation regarding the position and the number of hydroxy groups.

Preferably, $R^1$ and $R^2$ are linear and have hydroxyl groups at terminal. Examples of hydroxyalkyl groups having 2 to 5 carbon atoms include 2-hydroxyethyl, 3-hydroxypropyl, 4-hydroxybutyl, and 5-hydroxypentyl.

In the formula I, when $R^1$ and $R^2$ are —$(CH_2CH_2O)_mR^6$, m is an integer of 1 to 120, preferably 1 to 50. $R^6$ is a hydrogen atom, a methyl group, an ethyl group, or a propyl group. In this case, the average molecular weight of the $R^1$ and $R^2$ moiety is preferably about 45 to about 5000 (which corresponds to m of 1 to 120), and more preferably about 45 to about 2000 (which corresponds to m of 1 to 50).

In the formula I, when $R^1$ and $R^2$ are —$(CH_2CH_2NR^7)_mH$, m is an integer of 1 to 120, preferably 1 to 50. $R^7$ is an ethyl group or an N,N-dialkylaminoethyl group, and the number of carbon atoms of the alkyl is 2 to 5. In this case, the average molecular weight of the $R^1$ and $R^2$ moiety is preferably about 45 to about 5000 (which corresponds to m of 1 to 120), and more preferably about 45 to about 2000 (which corresponds to m of 1 to 50).

In the formula I, when $R^1$ and $R^2$ are alkyl groups having 6 to 20 carbon atoms, the alkyl groups can be linear, branched or cyclic, and preferably linear. For $R^1$ and $R^2$, examples of alkyl groups having 6 to 20 carbon atoms include n-hexyl, n-pentyl, n-octyl, n-nonyl, n-decyl, n-dodecyl and n-hexadecyl.

Regarding $R^1$ and $R^2$ in the formula I, in view of the fact that the dehydrating condensing agent of the present invention can be easily accumulated at the water interface, it is preferable that the $R^1O$— and $R^2O$— moieties are hydrophilic. It is preferable that at least one of $R^1$ and $R^2$ is a methyl group or an ethyl group, and more preferably both are methyl groups, although this depends on the combination with $R^3$, $R^4$ and $R^5$, which will be described in detail. It is not preferable that both $R^1$ and $R^2$ are alkyl groups having 6 to 20 carbon atoms at the same time, because the hydrophobicity of the dehydrating condensing agent of the present invention becomes strong, which makes accumulation of the condensing agent at the water interface difficult.

In —$CH_2COO$—$C_nH_{2n+1}$, —$C_nH_{2n+1}$, or —$C_6H_4$-p-$C_nH_{2n+1}$, which can be $R^3$, $R^4$ and $R^5$ in the formula I, n is an integer of 6 to 20, and —$C_nH_{2n+1}$ is linear. Examples thereof include n-octyloxycarbonyl methylene, n-decyloxycarbonyl methylene, n-dodecyloxycarbonyl methylene, n-hexadecyloxycarbonyl methylene; n-hexyl, n-heptyl, n-octyl, n-nonyl, n-decyl, n-undecyl, n-dodecyl, n-tridecyl, n-tetradecyl, n-pendadecyl, n-hexadecyl, n-heptadecyl, n-octadecyl, n-nonadecyl, n-eicocyl; p-(n-hexyl)phenylene, p-(n-octyl)phenylene, p-(n-decyl)phenylene, p-(n-dodecyl)phenylene, p-(n-tetradecyl)phenylene, p-(n-hexadecyl)phenylene, and p-(n-octadecyl)phenylene. In view of the retention of the dehydrating condensing agent of the present invention at the water interface, it is preferable that n is 8 to 18, and more preferably 12 to 16.

Regarding $R^3$, $R^4$ and $R^5$ in the formula I, in view of the fact that the dehydrating condensing agent of the present invention can be easily synthesized and readily accumulated at the water interface, it is preferable that one or two of $R^3$, $R^4$ and $R^5$ are methyl groups, and the remaining $R^3$, $R^4$ and $R^5$ are groups having linear alkyl groups having 6 to 20 carbon atoms. In view of reactivity, it is more preferable that two of $R^3$, $R^4$ and $R^5$ are methyl groups. It is not preferable that all of $R^3$, $R^4$ and $R^5$ are groups having linear alkyl groups having 6 to 20 carbon atoms, because the reaction efficiency is not good.

Examples of the halide ion of $X^-$ in the formula I include $F^-$, $Cl^-$, $Br^-$ and $I^-$. Examples of R in the sulfonate ion ($RSO_3^-$) in the formula I include a methyl group, an ethyl group, a phenyl group, and a p-tolyl group. It is preferable that $X^-$ is $Cl^-$ or a triflate anion in view of ease of synthesis of the dehydrating condensing agent of the present invention.

The dehydrating condensing agent of the present invention represented by the above formula I can be produced, for example, by the method described in the following scheme 1 or 2.

First, scheme 1 will be described.

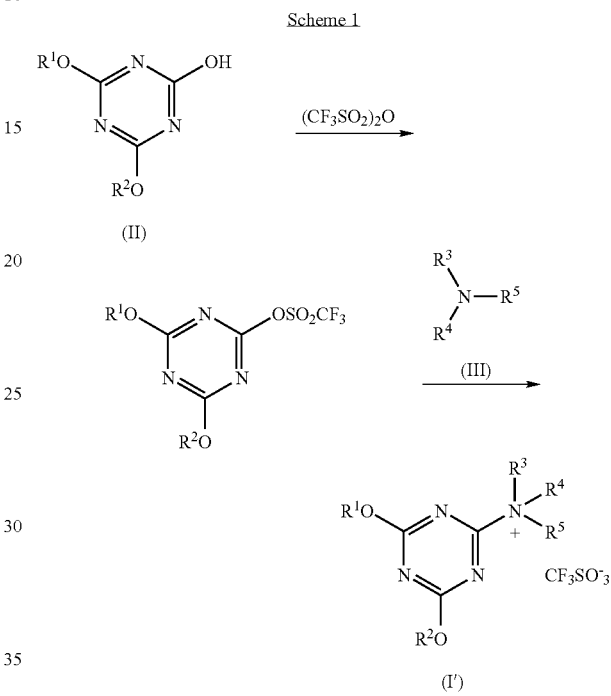

In the scheme 1, $R^1$ to $R^5$ are the same as those defined regarding the formula I.

This method can be performed according to the method reported by Kunishima et al. (Tetrahedron Letters, 2002, vol. 43, pp. 3323-3326). More specifically, this includes the steps of mixing a compound represented by the formula II (2-hydroxy-4,6-dimethoxy-1,3,5-triazine) and trifluoromethanesulfonic anhydride in an organic solvent to obtain a triflate; and mixing the obtained triflate and a tertiary amine represented by the following formula III in an appropriate organic solvent.

In the step of obtaining a triflate, trifluoromethanesulfonic anhydride is used preferably in about 1 to 2 equivalents, more preferably 1 to 1.5 equivalents, with respect to the compound II. The organic solvent used in this step include dichloromethane, chloroform, carbon tetrachloride, pentane, hexane, petroleum ether, benzene, and toluene, and dichloromethane is preferable. It is more preferable to add N,N-diisopropylethylamine in an equivalent substantially equal to the compound II to promote the reaction. The reaction can be performed at room temperature, and is generally performed for 30 min to 6 hours. More preferably, the reaction is performed in an nitrogen atmosphere.

Next, the obtained triflate and the tertiary amine of the formula III are mixed. The tertiary amine is used preferably in about 1.5 to 3 equivalents with respect to the compound II, which is the starting material. Preferable examples of the organic solvent used in this step include tetrahydrofuran (THF), acetonitrile, dichloromethane, and chloroform. The reaction can be performed at room temperature, and is generally performed for 15 min to 3 hours.

Thus, the compound I' in which X⁻ is a triflate anion of the dehydrating condensing agent of the present invention represented by the formula I can be obtained in a high yield.

Next, the scheme 2 will be described.

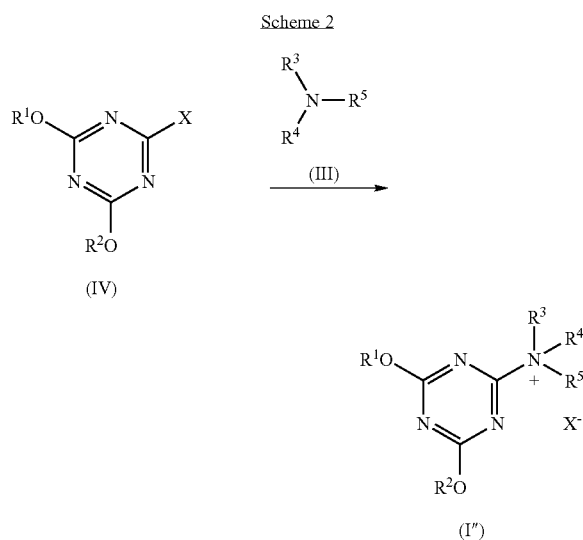

Scheme 2

In the scheme 2, $R^1$ to $R^5$ are the same as those defined regarding the formula I, and X is a halogen atom.

This method includes the step of mixing a compound represented by the formula IV and the tertiary amine represented by the formula III in an appropriate solvent. The tertiary amine is used preferably in about 1.5 to 3 equivalents with respect to the compound IV, which is the starting material. There is no particular limitation on the solvent used in this step, as long as it is a neutral solvent. Specific examples thereof include methanol, ethanol, 2-propanol, dimethylsulfoxide, N,N-dimethylformamide, tetrahydrofuran (THF), acetonitrile, and their appropriately mixed solvents; diethyl ether, methylene chloride, chloroform, ethyl acetate, and hexane, and tetrahydrofuran (THF) is preferable. The solvents used in this step may be water, a buffer solution (phosphate buffer, Tris-hydrochloride buffer, carbonate buffer, etc.), and a mixture with the aforementioned solvents that is miscible with these buffer. The reaction can be performed at room temperature, and is generally performed for 15 min to 3 hours.

Thus, the compound I" in which X− is a halide anion of the dehydrating condensing agent of the present invention represented by the formula I can be obtained in a high yield.

When X− in the formula I is a nitrate ion, the compound of the present invention can be obtained, for example, by anion exchange which may be preformed by adding silver nitrate to an aqueous solution of the halide represented by the formula I" and mixing them. When X− is a sulfate ion, a hydrogensulfate ion, a sulfonate ion, a tetrafluoroborate ion, or a perchlorate ion, the compound of the present invention can be produced in the same manner. For anion exchange, for example, ion exchange resin can be used, or treatment with excessive salts can be performed.

The dehydrating condensing agent of the present invention can be used preferably when producing carboxylic acid derivatives from carboxylic compounds and compounds having nucleophilic functional groups such as >NH groups, —OH groups, —SH groups. In particular, when producing amide compounds from carboxylic acid compounds and amine compounds, or when producing ester compounds from carboxylic acid compounds and alcohol compounds, the dehydrating condensing agent of the present invention can be used preferably in an aqueous solution.

When producing carboxylic acid derivatives using the dehydrating condensing agent of the present invention, the mechanism of the dehydrating condensation can be as follows. Since the dehydrating condensing agent of the present invention has at least one medium or long chain alkyl group in the quaternary ammonium structure, it is amphiphilic, and can form micelles in an aqueous solution, or can be incorporated preferentially into micelles that are formed by another surfactant. At this time, for example, since the carboxylic acid compound, which is the substrate, also has a hydrophobic moiety, it can form micelles together with the dehydrating condensing agent, or can be incorporated preferentially into micelles that are formed by another surfactant. Therefore, the concentration of the quaternary ammonium moiety of the dehydrating condensing agent of the present invention and the concentration of the carboxyl group of the carboxylic acid compound at the water interface are much higher than those in the solution or the aggregation. Therefore, the carboxyl group is activated by being added to the triazino group to which the quaternary ammonium cation is bonded, and causes dehydration with the nucleophilic functional groups of the amine compounds or the alcohol compounds in the aqueous solution, so that amide compounds or ester compounds can be generated. The molecular aggregate phase formed herein may be micelles having any shape, and can be spherical or layered. The same effect can be expected at a water interface (surface) of a membrane such as lipid bilayer, gel-like hydrated solid, or emulsion to which an organic solvent that is immiscible with water is added.

There is no particular limitation on carboxylic acid compounds used in the method for producing carboxylic acid derivatives of the present invention, as long as they are amphiphilic carboxylic acids having an ability of accumulating at the water interface. Such carboxylic acids are preferably carboxylic acids having fat-soluble groups such as long chain alkyl groups, more preferably linear, branched, or cyclic carboxylic acids having about 10 to about 20 carbon atoms. Specific examples include capric acid (decanoic acid), undecanoic acid, lauric acid (dodecylic acid), myristic acid, palmitic acid, palmitoleic acid, stearic acid, oleic acid, elaidic acid, petroselinic acid, linoic acid, α-linolenic acid, γ-linolenic acid, icosanic acid, icosatrienic acid, and arachidonic acid. These carboxylic acid compounds can be generally provided in the form of a sodium salt, potassium salt or the like. Alternatively, when a carboxylic acid having no or insufficient (low) fat-solubility is used, emulsion can be used to which an organic solvent immiscible with water (e.g., aromatic or aliphatic hydrocarbon solvents such as toluene, benzene, xylene, pentane, hexane, heptane, and octane; halogenized solvents such as methylene chloride, chloroform, and carbon tetrachloride; ester solvents such as ethyl acetate; ether solvents such as diethyl ether, and butyl methyl ether) is added. Alternatively, such carboxylic acid compounds can be converted into carboxylic acid compounds that can be accumulated at the water interface by introducing a long alkyl group as described above into them via any chemical bond. Herein, examples of the chemical bonds include ester, acid amide, ether, ester carbonate, and urethane, and the long chain alkyl group can be introduced into the carboxylic acid compound by a method routinely used by those skilled in the art. Thus, carboxylic acid compounds that have inherently no fat-solubility can be incorporated into the water interface, and thereby a dehydrating condensation can be performed.

There is no particular limitation on the amine compounds that can be used in the method for producing carboxylic acid derivatives of the present invention. There is no particular limitation, preferably, as long as they are compounds having amphiphilic primary or secondary amino groups having an ability of accumulating at the water interface. Examples of such amine compounds include aliphatic amines (e.g., methylamine, ethylamine, propylamine, isopropylamine, n-butylamine, sec-butylamine, isobutylamine, tert-butylamine, n-pentylamine, n-hexylamine, n-octylamine, dimethylamine, diethylamine, diisopropylamine, allylamine, diallylamine, pyrrolidine, piperidine, 2-pipecoline, 3-pipecoline, 4-pipecoline, N-methylpiperazine); aromatic amines (e.g., aniline, benzylamine, α-phenethylamine, β-phenethylamine, 2-aminothiazole, 2-aminopyridine, 3-aminopyridine, 4-aminopyridine, indole); and amino acid derivatives whose carboxyl group is protected. These amine compounds generally can be provided in the form of an amine salt such as hydrochloride and nitrate. Alternatively, compounds having acid amide groups can be used. Such amine compounds are preferably amphiphilic amines having fat-solubility. For fat-insoluble amine compounds, fat-soluble groups (e.g., long chain alkyl group having about 10 to about 20 carbon atoms) may be introduced into the compounds via any chemical bond in the same manner as in the case of the carboxylic acid compounds.

There is no particular limitation on the alcohol compounds that can be used in the method for producing carboxylic acid derivatives of the present invention, as long as they are compounds having primary, secondary or tertiary hydroxyl groups and are amphiphilic compounds having an ability of accumulating at the water interface. Examples of such alcohol compounds include n-butanol, 1-hexanol, 1-octanol, capryl alcohol, decyl alcohol, lauryl alcohol, cetyl alcohol, phenol, o-cresol, m-cresol, p-cresol, benzyl alcohol, allyl alcohol, ethylene glycol, and glycerin. Furthermore, for fat-insoluble alcohol compounds, fat-soluble groups (e.g., long chain alkyl group having about 10 to about 20 carbon atoms) may be introduced into the compounds via any chemical bond in the same manner as in the case of the carboxylic acid compounds.

There is no particular limitation on the thiol compounds that can be used in the method for producing carboxylic acid derivatives of the present invention, as long as they are compounds having amphiphilic thiol groups having an ability of accumulating at the water interface. Examples of such thiol compounds include methane thiol, ethane thiol, benzene thiol, and cysteine derivatives. For fat-insoluble thiol compounds, fat-soluble groups (e.g., long chain alkyl group having about 10 to about 20 carbon atoms) may be introduced into the compounds via any chemical bond in the same manner as in the case of the carboxylic acid compounds.

There is no particular limitation on the amounts of the carboxylic acid compounds and the compounds having nucleophilic functional groups that are used in the method for producing carboxylic acid derivatives of the present invention. The reaction between carboxyl groups and nucleophilic functional groups proceeds stoichiometrically, so that the reaction can be determined depending on the number of the functional groups in each compound. For example, in the case of a reaction between compounds having one functional group each in a molecule, in general, the compound having a nucleophilic functional group is used in a ratio of 0.8 moles to 1.5 moles, preferably 0.9 moles to 1.2 moles, with respect to one mole of a carboxylic acid compound.

The method for producing carboxylic acid derivatives of the present invention includes a step of mixing the carboxylic acid compound and the compound having a nucleophilic functional group in an aqueous solution in the presence of the dehydrating condensing agent of the present invention. In this step, another surfactant may be included in the aqueous solution. There is no limitation on the order of mixing the compounds.

Examples of the aqueous solution used in this method include water, salt solution (e.g., sodium chloride aqueous solution, potassium chloride aqueous solution), and buffer solution (e.g., phosphate buffer, Tris-hydrochloride buffer). The pH of the aqueous solution is generally 6 to 11, preferably 7 to 8.5, although it depends on the compound to be used for reaction. In the case of salt solution and buffer solution, there is no particular limitation on the salt concentration in the solution, as long as it does not inhibit the reaction.

Examples of another surfactant that can be used in this method include anionic surfactants (e.g., sulfate ester such as sodium lauryl sulfate (SDS), sulfonate such as sodium dodecanesulfonate, phosphate ester); cationic surfactants (e.g., quaternary ammonium such as dodecyl trimethyl ammonium chloride); and neutral surfactants (e.g., nonionic surfactants such as alkyl polyoxyethylene ethers, zwitterionic surfactants such as phosphatidylcholine). Alternatively, phospholipid or artificial lipid that can form a lipid bilayer can be used.

In the method for producing carboxylic acid derivatives of the present invention, there is no particular limitation on the type and the amount of the dehydrating condensing agent of the present invention, as long as micelles can be formed in the aqueous solution, or the dehydrating condensing agent can be incorporated preferentially into the micelles formed by another surfactant. The amount that allows micelle formation can be determined as appropriate, referring to the critical micelle concentrations of the dehydrating condensing agent, the fatty acid salt, or another surfactant. In the case where an emulsion is formed, there is no particular limitation on the amount of the surfactant or the amount of the organic solvent, as long as an emulsion can be formed.

The above-described step can be determined as appropriate, depending on the compound used, and can be performed preferably at room temperature, more preferably at 20° C. to 30° C. There is no particular limitation on the reaction time, which is preferably 30 min to 24 hours, more preferably 1 to 6 hours.

Alternatively, when the compound of formula I" is used as the dehydrating condensing agent, it is possible to add the compound of the formula IV and the compound of the formula III, which are the raw materials of the compound of the formula I" of the dehydrating condensing agent of the present invention, at the same time to the reaction system between the carboxylic acid compound and the compound having a nucleophilic functional group, which are the raw materials of the targeted carboxylic acid derivatives.

The carboxylic acid derivatives obtained in this manner can be separated and purified by methods routinely used by those skilled in the art. For example, after the reaction is completed, an organic solvent is added to the reaction mixture, and the resultant carboxylic acid derivative is extracted to the organic layer, and then purified by chromatography or the like.

EXAMPLES

Example 1

Synthesis of Dodecyl Chain-Containing Condensing Agent

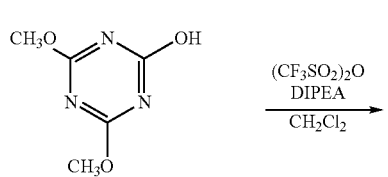

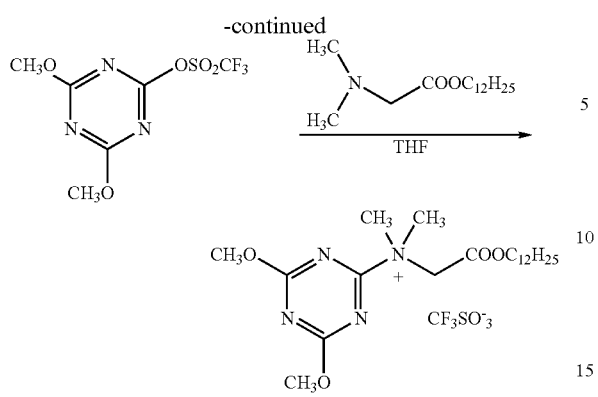

Trifluoromethanesulfonic anhydride (0.57 g, 2.30 mmol) and N,N-diisopropylethylamine (DIPEA) (0.24 g, 1.84 mmol) were added to a solution of 2-hydroxy-4,6-dimethoxy-1,3,5-triazine (0.29 g, 1.84 mmol) in methylene chloride (40 mL) at room temperature. After one hour with stirring at room temperature, the reaction mixture was transferred into a separatory funnel, and the organic layer was washed with water three times, and dried over magnesium sulfate, and then concentrated under reduced pressure. The residue was dissolved in tetrahydrofuran (THF) (4 mL), and then a solution of N,N-dimethylglycine dodecyl ester (0.2 g, 0.74 mmol) in THF (6 mL) was added thereto, followed by stirring at room temperature for 30 min. The reaction mixture was concentrated under reduced pressure, and the resulting residue was purified by decantation with hexane and diethyl ether to give a dodecyl chain-containing condensing agent (amount: 0.26 g; yield: 63%).

2-(N-(4,6-dimethoxy-1,3,5-triazin-2-yl)-N,N-dimethylammonio) acetate 1-dodecyl ester trifluoromethanesulfonic acid: colorless crystal, melting point: 52-54° C., NMR (CDCl$_3$) δ 0.88 (t, J=6.9, 3H), 1.23-1.34 (m, 18H), 1.63 (quint, J=6.8, 2H), 3.80 (s, 6H), 4.14 (t, J=6.8, 2H), 4.17 (s, 6H), 5.11 (s, 2H), element analysis for $C_{22}H_{39}F_3N_4O_7S$: Calculated: H, 7.01; C, 47.13; N, 9.99. Found: H, 7.08; C, 46.97; N, 10.04.

Example 2

Synthesis of Octyl Chain-Containing Condensing Agent

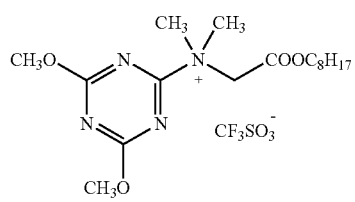

The same procedure as in Example 1 was performed except that N,N-dimethylglycine octyl ester was used instead of N,N-dimethylglycine dodecyl ester to give an octyl chain-containing condensing agent in 75% yield.

2-(N-(4,6-dimethoxy-1,3,5-triazin-2-yl)-N,N-dimethylammonio) acetate 1-octyl ester trifluoromethanesulfonic acid: colorless crystal, melting point: 51-53° C., NMR (CDCl$_3$) δ 0.88 (t, J=6.9, 3H), 1.23-1.33 (m, 10H), 1.63 (quint, J=6.8, 2H), 3.79 (s, 6H), 4.14 (t, J=6.8, 2H), 4.17 (s, 6H), 5.10 (s, 2H), element analysis for $C_{18}H_{31}F_3N_4O_7S$: Calculated: H, 6.19; C, 42.85; N, 11.10. found: H, 5.93; C, 42.67; N, 11.16.

Example 3

Synthesis of Hexadecyl Chain-Containing Condensing Agent

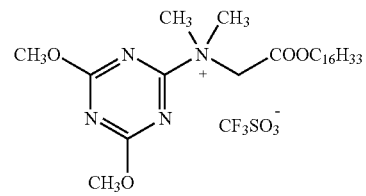

The same manner as in Example 1 was performed except that N,N-dimethylglycine hexadecyl ester was used instead of N,N-dimethylglycine dodecyl ester to give a hexadecyl chain-containing condensing agent in 73% yield.

2-(N-(4,6-dimethoxy-1,3,5-triazine-2-yl)-N, N-dimethylammonio) acetate 1-hexadecyl ester trifluoromethanesulfonic acid: colorless crystal, melting point: 59-61° C., NMR (CDCl$_3$) δ 0.88 (t, J=6.9, 3H), 1.23-1.33 (m, 26H), 1.63 (m, 2H), 3.79 (s, 6H), 4.14 (t, J=6.8, 2H), 4.17 (s, 6H), 5.10 (s, 2H), element analysis for $C_{26}H_{47}F_3N_4O_7S$—$H_2O$: Calculated: H, 7.78; C, 49.20; N, 8.83. found: H, 7.61; C, 49.50; N, 9.38.

Comparative Example 1

Synthesis of Ethyl Chain-Containing Condensing Agent

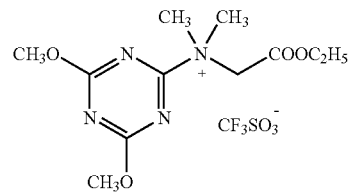

The same manner as in Example 1 was performed except that N,N-dimethylglycine ethyl ester was used instead of N,N-dimethylglycine dodecyl ester to give an ethyl chain-containing condensing agent in 79% yield.

2-(N-(4,6-dimethoxy-1,3,5-triazin-2-yl)-N,N-dimethylammonio) acetate ethyl ester trifluoromethanesulfonic acid: white powder, melting point: 52-56° C., NMR (CDCl$_3$) δ 1.29 (t, J=7.1, 3H), 3.79 (s, 6H), 4.17 (s, 6H), 4.21 (q, J=7.1, 2H), 5.10 (s, 2H).

Example 4

Dehydrating Condensation of Sodium Laurate and N-Butylamine Using Octyl Chain-Containing Condensing Agent

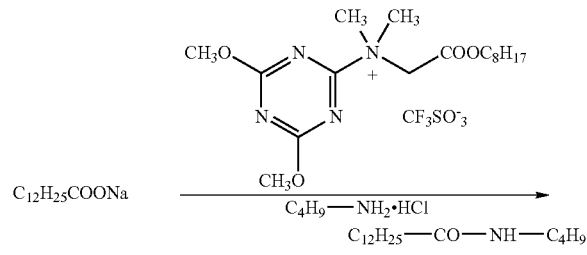

A total volume of 2 mL of 20 mM phosphate buffer solution (pH 8) containing 15 mM sodium laurate, 20 mM n-butylamine hydrochloride and 1.5 mM octyl chain-containing condensing agent obtained in Example 2 was stirred at 25° C. for 0.5 min, 0.75 min, or 1 min. In the reaction mixture, micelle formation was observed. After a predetermined time, 0.3 mL of 1M hydrochloric acid was added to stop the reaction, and allowed to stand for 10 minutes. Then, 20 mL of ethyl acetate was added thereto, followed by stirring, and then the ethyl acetate layer was collected, and concentrated with an evaporator. A small amount of ethyl acetate was added to the resultant residues so as to dissolve the residues completely, and an internal standard (n-hexacosane) was added thereto and the product was determined by gas chromatography (GC). The same operation was repeated twice or more. The analysis conditions of GC were as follows:

Apparatus: Shimadzu GC-14B
Column: Carrier: silica gel Silicone OV-17 (manufactured by GL Sciences Inc.),
    Length: 2 m, internal diameter 3.2 mm
Column temperature : 200° C.
Injection temperature: 230° C.
Detection temperature: 230° C.

The average yield in each period of time of the obtained N-butyldodecanamide was 41.4% for 0.5 min, 64.8% for 0.75 min, and 74.5% for 1 min. The concentration of the remaining raw material was calculated from the yield of the product of each period of time, and a pseudo-first-order rate constant (k) was calculated by the linear least square method from the following equation:

$$ln[S]/ln[S]_0 = -kt$$

where t is the reaction time (min), [S] is the concentration of the condensing agent at time t, and $[S]_0$ is the concentration of the condensing agent at time 0 (initial concentration). In this example, $k=1.39$ min$^{-1}$.

On the other hand, a comparative experiment of a monodisperse system in which micelles are not formed was performed in the same reaction system where in the above dehydrating condensation reaction, sodium butyrate was used instead of sodium laurate, and an ethyl chain-containing condensing agent obtained in Comparative Example 1 was used as the condensing agent. The reaction time was 15 min, 30 min, and 60 min. The average yield of N-butylbutanamide obtained in each period of time was 2.9% for 15 min, 4.3% for 30 min, and 7.4% for 60 min, and $k=1.2\times10^{-3}$ min$^{-1}$. Therefore, the reaction rate of the former in which micelles are formed was 1160 times higher than the latter in the monodisperse system.

Example 5

Dehydrating Condensation Reaction of Various Fatty Acids and Amine (1)

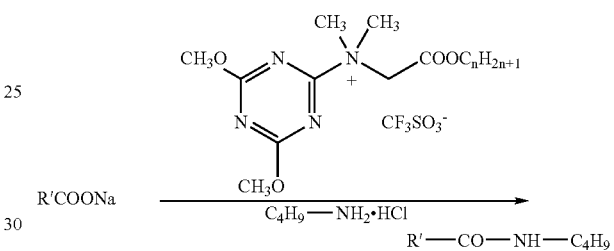

A total volume of 2 mL of 20 mM phosphate buffer solution (pH 8) containing 15 mM of various types of fatty acid sodium salt described in Table 1 below, 20 mM n-butylamine hydrochloride and 1.5 mM of various condensing agents described in Table 1 below was stirred at 25° C. for an optional time. After the reaction was terminated, the product was determined by gas chromatography (GC) in the same manner as in Example 4. The ratio of relative rate in stoichiometric reaction of each product is shown in Table 1. It should be noted that only in the case of sodium stearate, the concentration of n-butylamine hydrochloride was 5 mM.

TABLE 1

| | Carboxylic acid salt (R'COONa) | | | | |
|---|---|---|---|---|---|
| Condensing agent | Na-Butyrate (C4) | Na-Octate (C8) | Na-Laurate (C12) | Na-Oleate (C18) | Na-Stearate (C18) |
| [structure] | 1* | 1 | 36 | 52 | 19 |

TABLE 1-continued

| Condensing agent | Carboxylic acid salt (R'COONa) | | | | |
|---|---|---|---|---|---|
| | Na-Butyrate (C4) | Na-Octate (C8) | Na-Laurate (C12) | Na-Oleate (C18) | Na-Stearate (C18) |
| 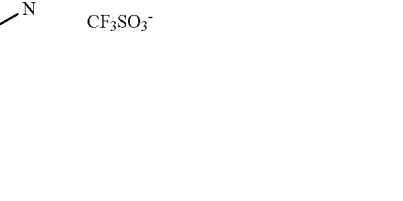 | 1 | 3 | 980 | 580 | 270 |
| 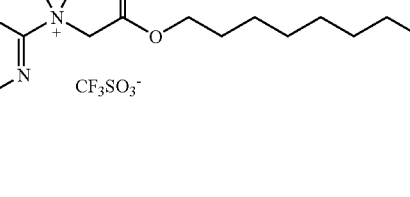 | 17 | 235 | 660 | 700 | 410 |
| 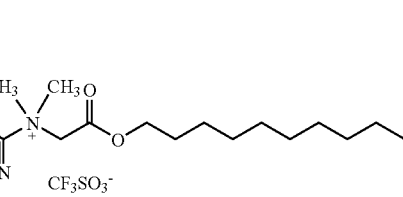 | 33 | 340 | 1260 | 580 | 270 |
| Nature of reaction mixture | Mono-disperse | Mono-disperse | Micelle | Micelle | Gel |

*Pseudo-first-order rate constant $k = 1.0 \times 10^{-3}$ (min$^{-1}$)

In the case where the alkyl chain of the condensing agent is short, the relative rate in the stoichiometric reaction was slow. In the case of carboxylic acid compounds, it is recognized that the longer the length of hydrocarbon chain is, the faster the relative rate is. In particular, the relative rate of the reaction under micelle formation was at least 1000 times faster than that of the monodisperse system (the case of the reaction of ethyl chain-containing condensing agent and sodium butyrate). This indicates that micelle formation increases the reaction rate significantly.

Example 6

Dehydrating Condensation Reaction of Various Fatty Acids and Amines (2)

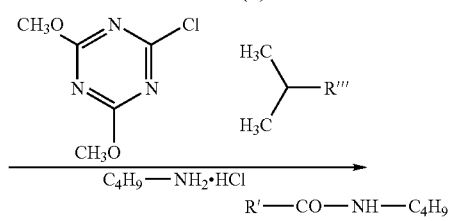

A total volume of 2 mL of 20 mM phosphate buffer solution (pH 8) containing 15 mM of various types of sodium fatty acids described in Table 2 below, 20 mM n-butylamine hydrochloride, 15 mM 2-chloro-4,6-dimethoxy-1,3,5-triazine, and 1.5 mM of tertiary amine described in Table 2 below was stirred at 25° C. for an optional time. After the reaction was terminated, the product was determined by gas chromatography in the same manner as in Example 4. The ratio of relative rate in stoichiometric reaction of each product is shown in Table 2.

TABLE 2

| Tertiary amine | Carboxylic acid salt (R'COONa) | |
| --- | --- | --- |
| | Na-Octate (C8) | Na-Laurate (C12) |
| CH$_3$–N(CH$_3$)–CH$_2$CH$_2$OH | 1.0* | 22 |
| CH$_3$–N(CH$_3$)–CH$_2$–C(=O)–O–CH$_2$CH$_3$ | 1.1 | 40 |
| CH$_3$–N(CH$_3$)–CH$_2$–C(=O)–O–(CH$_2$)$_{15}$CH$_3$ | — | 132 |
| Nature of reaction mixture | Monodisperse | Micelle |

*Pseudo-first-order rate constant $k = 8.1 \times 10^{-5}$ (min$^{-1}$)

Example 7

Competition Experiment of Carboxylic Acid

To 20 mM phosphate buffer (pH 8) containing 15 mM sodium laurate, 15 mM sodium butyrate, and 20 mM n-butylamine hydrochloride, 3 mM of the octyl chain-containing condensing agent obtained in Example 2 was added at 25° C. such that the total volume became 2 mL, and stirred at 25° C. for one hour. After the reaction was terminated, the product was determined by gas chromatography in the same manner as in Example 4.

The yield of N-butyldodecanamide, which is an amide of lauric acid, was 87.3%, and the yield of N-butylbutanamide, which is an amide of butyric acid, was 0.4%. The total yield was 87.7%. Thus, the reaction selectivity was lauric acid: butyric acid=99.6:0.4, which confirmed that the ratio of reaction rate is reflected on the yield.

Example 8

Dehydrating Condensation of Various Fatty Acids and Alcohols $$CH_3(CH_2)_9CH_2COONa \;+\;$$

$$CH_3(CH_2)_{10}CH_2OH \xrightarrow{\begin{array}{c} CH_3(CH_2)_6CH_2-O-C(=O)-CH_2-N^+(CH_3)_2-\text{triazine(OMe)}_2 \cdot \text{TfO}^- \end{array}}$$

$$CH_3(CH_2)_9CH_2COCH_2(CH_2)_{10}CH_3$$

To 6 mL of sodium laurate solution (50 mM), 12.1 mL of water was added to prepare a solution. To each of 1.81 mL of this solution, 0.04 mL of dodecanol (0.75 M) in acetone was added and then sonicated at 30° C. for 5 min. Then, 0.15 mL of 40% acetone solution in which the octyl chain-containing condensing agent (20 mM) obtained in Example 2 was contained was added thereto and stirred at 25° C. After 15 min, 30 min, 1 hour, 10 hours, and 24 hours from the start of the reaction, 5M hydrochloric acid (0.3 mL) was added to each reaction mixture to stop the reaction. The reaction mixture was transferred onto an Extrelut (2 g), and washed with water (0.2 mL), and then allowed to stand for 10 min. Ethyl acetate (20 mL) was allowed to flow onto the Extrelut, and then the eluate was distilled under reduced pressure. An internal standard (n-eicosane) in ethyl acetate was added to the residue and stirred sufficiently, and then determined by GC. The analysis conditions of GC were as follows:

Apparatus: Shimadzu GC-17A

Column: DB-5 (internal diameter 0.53 mm, length 30 m; manufactured by Agilent Technologies)

Column temperature: 260° C., which is the start temperature, was kept for one min, and then increased to 290° C. at a temperature rising rate of 20° C./min (1.5 min), and then 290° C. was kept for 3.5 min.

Injection temperature: 300° C.

Detection temperature: 300° C.

The average yield in each period of time of the obtained ester was 72% for 15 min, 62% for 30 min, 65% for one hour, 38% for 10 hours, and 39% for 24 hours. These results confirmed that the reaction at 25° C. had complete within 15 min.

In esterification by the dehydrating condensation that proceeds in a methanol solvent using DMT-MM, although as high concentration as about 25 M of methanol is used as a nucleophilic agent, the dehydrating condensation takes three hours at room temperature (Kunishima at al., Tetrahedron, 1999, vol. 55, pp. 13159-13170). On the other hand, in this example, although the concentration of the alcohol is only 15 mM, which is 1/1600 or less compared with the above concentration, the esterification is accelerated drastically. This seems to be due to interface effects such as the substrate being concentrated locally, and the substrate to be reacted being oriented favorably. Therefore, these results strongly suggest that a series of reactions proceed at micelle/water interfaces.

Furthermore, since the amount of ester generated decreases over time, it can be suggested that the reaction proceeds kinetically in a short time, after which, hydrolysis proceeds at the interface.

Example 9

Competition Experiment of Carboxylic Acid in Emulsion

First, 1% toluene (20 μL) was added to an aqueous solution containing sodium butyrate (10 μmol, 5 mM), sodium benzoate (10 μmol, 5 mM), butylamine hydrochloride (40 μmol, 20 mM), polyethylene glycol mono-4-octylphenyl ether (3 μmol, 1.5 mM) and phosphate buffer adjusted to pH 8 (40 μmol, 20 mM), and stirred to prepare an emulsion (cloudy). For comparison, a micelle solution without toluene and a solution without the surfactant and toluene were prepared. To each solution (1.85 mL), the octyl chain-containing condensing agent obtained in Example 2 (3 μmol, 1.5 mM) in 0.15 mL of 3% MeOH was added with stirring at 25° C. at 900 rpm. After 12 hours from the start of the reaction, the reaction was stopped by adding 5.0 M hydrochloric acid (0.3 mL). Each reaction mixture was transferred onto an Extrelut (2 g) and washed with water (0.2 mL) and then allowed to stand for 10 min. Ethyl acetate (20 mL) was allowed to flow onto the Extrelut, and then the eluate was distilled under reduced pressure. An internal standard (n-eicosane) in acetic acid solution was added to the residue and stirred sufficiently, and then the amount produced was determined by GC. The analysis conditions of GC were the same as in Example 4. The results are shown in Table 3.

TABLE 3

| | Surfactant | Toluene | Ratio of amide produced (from benzoate:from butyrate) | Yield |
|---|---|---|---|---|
| Emulsion system | 1.5 mM | 1% (20 μL) | 96:4 | 62% |
| Micelle system | 1.5 mM | 0 | 85:15 | 37% |
| Without surfactant | 0 mM | 0 | 55:45 | 10% |

In the condensation between carboxylic acid having a short chain length and amine, the yield and the selectivity were further improved in the emulsion system than in the micelle system.

INDUSTRIAL APPLICABILITY

The dehydrating condensing agent of the present invention increases the concentration of carboxylic acid, which is a substrate, at the water interface, and therefore the dehydrating condensation can be performed very efficiently. Furthermore, the dehydrating condensing agent of the present invention can be synthesized easily, and therefore is cost-efficient. The carboxylic acid derivatives produced in this manner can be used in a wide range of applications, for example, as pharmaceuticals, agricultural chemicals, dyes, or high molecular weight compounds. Among various pharmaceuticals or chemicals having various functional groups or being water-soluble, the agent of the present invention can be applied to synthesis of compounds having acid amide groups or ester groups.

The invention claimed is:

1. A 1,3,5-triazine compound represented by the following formula I:

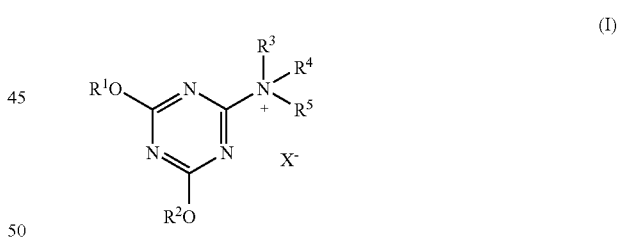

wherein $R^1$ and $R^2$ are each independently a methyl group, an ethyl group, a hydroxyalkyl group having 2 to 5 carbon atoms, $-(CH_2CH_2O)_m R^6$ (where m is an integer of 1 to 120, and $R^6$ is a hydrogen atom, a methyl group, an ethyl group, or a propyl group), $-(CH_2CH_2NR^7)_m H$ (where m is an integer of 1 to 120, and $R^7$ is an alkyl group having 2 to 5 carbon atoms, an N,N-dialkylaminoethyl group or $-CH_2CH_2N^+(CH_3)_3$), $-CH_2CH_2SO_3^-$, $-CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently $-CH_2COO-C_n H_{2n+1}$, $-C_n H_{2n+1}$, or $-C_6H_4$-p-$C_n H_{2n+1}$, where n is an integer of 6 to 20, and $-C_n H_{2n+1}$ is linear; and $X^-$ is a halide ion, a triflate anion, a nitrate ion, a sulfate ion, a hydrogensulfate ion, a sulfonate ion, a tetrafluoroborate ion, or a perchlorate ion.

2. The compound of claim 1, wherein at least one of $R^1$ and $R^2$ is a methyl group or an ethyl group.

3. The compound of claim 1, wherein n is 12 to 16.

4. A method for producing a 1,3,5-triazine compound represented by the following formula I':

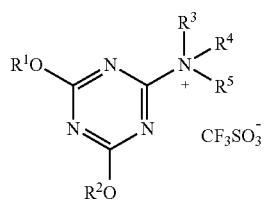

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear; and $X^-$ is an triflate anion, comprising:

obtaining triflate by mixing a compound represented by the following formula II and trifluoromethanesulfonic anhydride in an organic solvent:

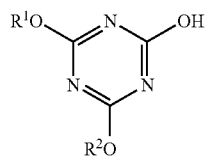

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and R is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; and mixing the obtained triflate and a tertiary amine represented by the following formula III in an appropriate organic solvent:

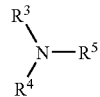

wherein one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear.

5. A method for producing a 1,3,5-triazine compound represented by the following formula I":

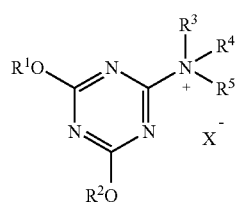

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear; and $X^-$ is a halide ion, comprising:

mixing a compound represented by the following formula IV and a tertiary amine represented by the following formula III in an appropriate solvent:

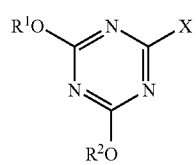

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; and X is a halogen atom;

(III)

wherein one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear.

6. A method for producing a carboxylic acid derivative, comprising:

mixing a carboxylic acid and a compound having a nucleophilic functional group in an aqueous solution in the presence of a 1,3,5-triazine compound represented by the following formula I:

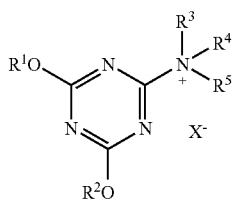
(I)

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is integer of 6 to 20, and —$C_nH_{2n+1}$ is linear; and $X^-$ is a halide ion, a triflate anion, a nitrate ion, a sulfate ion, a hydrogensulfate ion, a sulfonate ion, a tetrafluoroborate ion, or a perchlorate ion.

7. The method of claim 6, wherein the carboxylic acid is a fatty acid having 6 to 20 carbon atoms.

8. The method of claim 7, wherein the carboxylic acid is a fatty acid having 8 to 18 carbon atoms.

9. The method of claim 6, wherein at least one of $R^1$ and $R^2$ in the formula I is a methyl group or an ethyl group.

10. The method of claim 6, wherein n in the formula I is 12 to 16.

11. The method of claim 6, wherein the compound having a nucleophilic functional group is a primary amine compound or a secondary amine compound.

12. A method for producing a carboxylic acid derivative, comprising mixing:
a carboxylic acid;
a compound having a nucleophilic functional group;
a compound represented by the following formula IV; and
a tertiary amine represented by the following formula III in an aqueous solution:

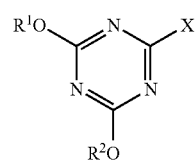
(IV)

wherein $R^1$ and $R^2$ are each independently a methyl group, an ethyl group, a hydroxyalkyl group having 2 to 5 carbon atoms, —$(CH_2CH_2O)_mR^6$ (where m is an integer of 1 to 120, and $R^6$ is a hydrogen atom, a methyl group, an ethyl group, or a propyl group), —$(CH_2CH_2NR^7)_mH$ (where m is an integer of 1 to 120, and $R^7$ is an alkyl group having 2 to 5 carbon atoms, an N,N-dialkylaminoethyl group or —$CH_2CH_2N^+(CH_3)_3$), —$CH_2CH_2SO_3^-$, —$CH_2CH_2N^+(CH_3)_3$, or an alkyl group having 6 to 20 carbon atoms, but both $R^1$ and $R^2$ are not alkyl groups having 6 to 20 carbon atoms at the same time; and X is a halogen atom,

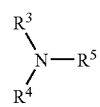
(III)

wherein one or two of $R^3$, $R^4$ and $R^5$ are methyl groups, and the remaining $R^3$, $R^4$ and $R^5$ are each independently —$CH_2COO$—$C_nH_{2n+1}$, —$C_nH_{2n+1}$, or —$C_6H_4$-p-$C_nH_{2n+1}$, where n is an integer of 6 to 20, and —$C_nH_{2n+1}$ is linear.

13. The method of claim 12, wherein the carboxylic acid is a fatty acid having 6 to 20 carbon atoms.

14. The method of claim 13, wherein the carboxylic acid is a fatty acid having 8 to 18 carbon atoms.

15. The method of claim 12, wherein at least one of $R^1$ and $R^2$ in the formula I is a methyl group or an ethyl group.

16. The method of claim 12, wherein n in the formula III is 12 to 16.

17. The method of claim 12, wherein the compound having a nucleophilic functional group is a primary amine compound or secondary amine compound.

18. The method of claim 12, wherein the compound having a nucleophilic functional group is an alcohol compound.

* * * * *